United States Patent
Dweck et al.

(10) Patent No.: US 6,520,036 B1
(45) Date of Patent: Feb. 18, 2003

(54) SAMPLE REMOVAL APPARATUS

(76) Inventors: David Dweck, 4141 N. 39th Ave., Hollywood, FL (US) 33021; Nir Hus, 4141 N. 39th Ave., Hollywood, FL (US) 33021

( * ) Notice: Subject to any disclaimer, the term of this patent is extended or adjusted under 35 U.S.C. 154(b) by 301 days.

(21) Appl. No.: 09/621,479
(22) Filed: Jul. 21, 2000
(51) Int. Cl.[7] .................................................. G01N 1/00
(52) U.S. Cl. .................................................. 73/864.44
(58) Field of Search ........................ 73/864.41, 864.44, 73/864.45; 204/615–617

(56) References Cited

U.S. PATENT DOCUMENTS

| | | |
|---|---|---|
| 3,814,079 A | 6/1974 | Le Roy, Sr. |
| D286,570 S | 11/1986 | Williams |
| 4,671,123 A | 6/1987 | Magnussen, Jr. et al. |
| 4,767,415 A | 8/1988 | Duffy |
| 4,933,148 A | 6/1990 | Perlman |
| 5,560,373 A | * 10/1996 | De Santis |
| 5,821,436 A | 10/1998 | Bienhaus et al. |

* cited by examiner

*Primary Examiner*—Robert Raevis

(57) ABSTRACT

A sample removal apparatus for excising and ejecting a section of a gel sample from a tray. The sample removal apparatus includes a chamber member that defines an chamber interior. The chamber member has a top with a perimeter wall depending therefrom. The perimeter wall has a lower cutting edge defining a cutting perimeter. The sample removal apparatus also includes a pipetor adapter for receiving a portion of a pipetor. The pipetor adapter has a receiving cavity for receiving the pipetor. A peripheral wall that has a lower end mounted to the top of the chamber member forms the receiving cavity.

20 Claims, 1 Drawing Sheet

SAMPLE REMOVAL APPARATUS

BACKGROUND OF THE INVENTION

1. Field of the Invention

The present invention relates to apparatuses and methods to extract a sample and more particularly pertains to a new sample removal apparatus for excising and ejecting a section of a gel sample from a tray.

2. Description of the Prior Art

The use of apparatuses and methods to extract a sample is known in the prior art. More specifically, apparatuses and methods to extract a sample heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,821,436; U.S. Pat. No. 4,671,123; U.S. Pat. No. 3,814,079; U.S. Pat. No. 4,933,148; U.S. Pat. No. 4,767,415; and U.S. Pat. No. Des. 286,570.

While these devices fulfill their respective, particular objectives and requirements, the aforementioned patents do not disclose a new sample removal apparatus. The inventive device includes a chamber member that defines an chamber interior. The chamber member has a top with a perimeter wall depending therefrom. The perimeter wall has a lower cutting edge defining a cutting perimeter. The sample removal apparatus also includes a pipetor adapter for receiving a portion of a pipetor. The pipetor adapter has a receiving cavity for receiving the pipetor. A peripheral wall that has a lower end mounted to the top of the chamber member forms the receiving cavity.

In these respects, the sample removal apparatus according to the present invention substantially departs from the conventional concepts and designs of the prior art, and in so doing provides an apparatus primarily developed for the purpose of excising and ejecting a section of a gel sample from a tray.

SUMMARY OF THE INVENTION

In view of the foregoing disadvantages inherent in the known types of apparatuses and methods to extract a sample now present in the prior art, the present invention provides a new sample removal apparatus construction wherein the same can be utilized for excising and ejecting a section of a gel sample from a tray.

The general purpose of the present invention, which will be described subsequently in greater detail, is to provide a new sample removal apparatus and method which has many of the advantages of the apparatuses and methods to extract a sample mentioned heretofore and many novel features that result in a new sample removal apparatus which is not anticipated, rendered obvious, suggested, or even implied by any of the prior art apparatuses and methods to extract a sample, either alone or in any combination thereof.

To attain this, the present invention generally comprises a chamber member that defines an chamber interior. The chamber member has a top with a perimeter wall depending therefrom. The perimeter wall has a lower cutting edge defining a cutting perimeter. The sample removal apparatus also includes a pipetor adapter for receiving a portion of a pipetor. The pipetor adapter has a receiving cavity for receiving the pipetor. A peripheral wall that has a lower end mounted to the top of the chamber member forms the receiving cavity.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new sample removal apparatus and method which has many of the advantages of the apparatuses and methods to extract a sample mentioned heretofore and many novel features that result in a new sample removal apparatus which is not anticipated, rendered obvious, suggested, or even implied by any of the prior art apparatuses and methods to extract a sample, either alone or in any combination thereof.

It is another object of the present invention to provide a new sample removal apparatus that may be easily and efficiently manufactured and marketed.

It is a further object of the present invention to provide a new sample removal apparatus that is of a durable and reliable construction.

An even further object of the present invention is to provide a new sample removal apparatus which is susceptible of a low cost of manufacture with regard to both materials and labor, and which accordingly is then susceptible of low prices of sale to the consuming public, thereby making such sample removal apparatus economically available to the buying public.

Still yet another object of the present invention is to provide a new sample removal apparatus which provides in the apparatuses and methods of the prior art some of the advantages thereof, while simultaneously overcoming some of the disadvantages normally associated therewith.

Still another object of the present invention is to provide a new sample removal apparatus for excising and ejecting a section of a gel sample from a tray.

Yet another object of the present invention is to provide a new sample removal apparatus which includes a chamber member that defines a chamber interior. The chamber member has a top with a perimeter wall depending therefrom. The perimeter wall has a lower cutting edge defining a cutting perimeter. The sample removal apparatus also includes a pipetor adapter for receiving a portion of a pipetor. The pipetor adapter has a receiving cavity for receiving the pipetor. A peripheral wall that has a lower end mounted to the top of the chamber member forms the receiving cavity.

Still yet another object of the present invention is to provide a new sample removal apparatus that excises an exact volume of gel.

Even still another object of the present invention is to provide a new sample removal apparatus that allows the user to avoid having to directly touch the agarose gel.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
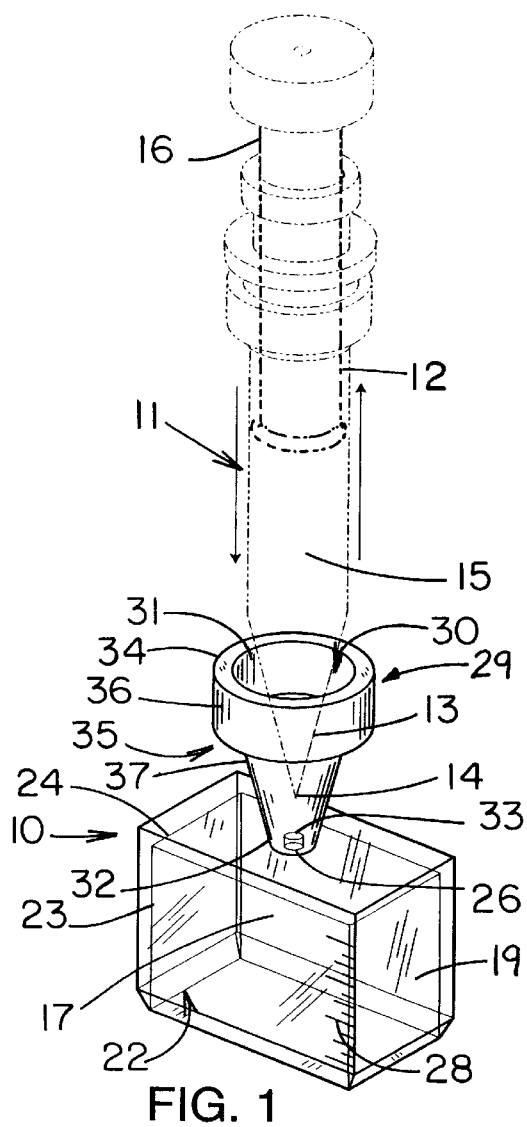
FIG. 1 is a schematic perspective view of a new sample removal apparatus according to the present invention, illustrating how the pipetor is inserted into the receiving cavity of the sample removal apparatus.
Figure 2:
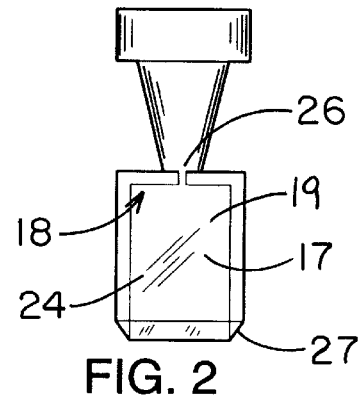
FIG. 2 is a schematic side view of the present invention.
Figure 3:
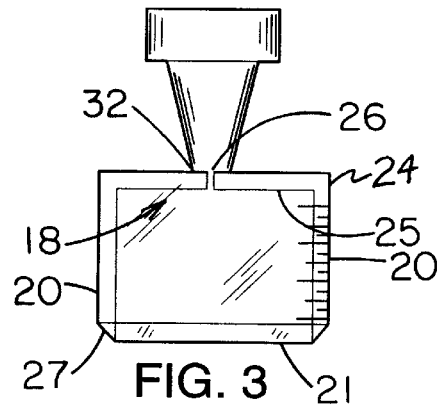
FIG. 3 is a schematic front view of the present invention.
Figure 4:
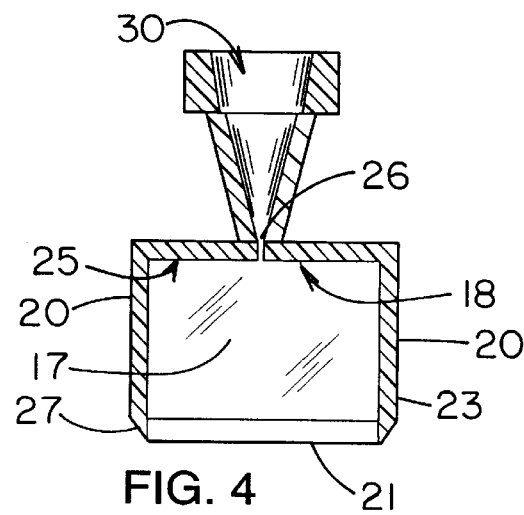
FIG. 4 is a schematic cross-section view of the present invention.

With reference now to the drawings, and in particular to FIGS. 1 through 4 thereof, a new sample removal apparatus embodying the principles and concepts of the present invention and generally designated by the reference numeral 10 will be described.

As best illustrated in FIGS. 1 through 4, the sample removal apparatus 10 is used in conjunction with a pipetor 11 for excising and ejecting a section of an agarose gel sample from a tray produced by agarose gel electrophoresis. The pipetor 11 is of the type that has a tubular member 12 with a frusta-conical end portion 13 with a tip aperture 14 that is in communication with a lumen 15 of the tubular member 12. In addition, the pipetor 11 is of the type that has a plunger 16 movable in the lumen 15 of the tubular member 12.

The sample removal apparatus 10 generally comprises a chamber member 19 that defines a chamber interior 17. The chamber member 19 has a top 18 and perimeter walls 20 that depend from the top 18. The perimeter walls 20 have a lower cutting edge 21. Moreover, the perimeter walls 20 are comprised of side walls 23 and end walls 24. The side walls 23 and end walls 24 define a substantially rectangular cutting perimeter 22 for excising a substantially rectangular section of a sample.

The chamber member 19 has a top wall 25 connected to the perimeter wall 20 opposite the lower cutting edge 21. The top wall 25 has an opening 26 therein that is in communication with the chamber interior 17. The lower cutting edge 21 of the perimeter wall is beveled to form a linear edge 27 designed for moving through gel of a sample. A plurality of graduations 28 are marked on the perimeter wall 20 that extend from the lower cutting edge 21 for indicating the volume of the gel section contained in the chamber interior 17. The chamber member 19 is made of a transparent material to facilitate the determination of the volume of gel section in the chamber interior 17.

The sample removal apparatus 10 also has a pipetor adapter 29 designed for receiving a portion of a pipetor 11. The pipetor adapter 29 has a receiving cavity 30 for receiving the portion of the pipetor 11. The receiving cavity 30 is formed by a peripheral wall 31 that has a lower end 32 mounted to the top 18 of the chamber member 19. The receiving cavity 30 has a hole 33 in communication with the opening 26 in the top wall 25 of the chamber member 19.

The peripheral wall 31 of the receiving cavity 30 is generally frusta-conical in shape. The peripheral wall 31 has an upper end 34 with a lip 35 formed thereon. The lip 35 has an outer surface 36 that protrudes from an exterior surface 37 of the peripheral wall 31 for facilitating the mounting of a pipetor on the pipetor adapter 29 of the sample removal apparatus, and the subsequent removal of the pipetor from the pipetor adapter of the sample removal apparatus. This is especially useful for helping the user avoid touching of the sample removal apparatus.

In use, the pipetor is mounted on the sample removal apparatus by inserting the end portion 13 of the pipetor 11 into the receiving cavity 30 of pipetor adapter 29 thereby engaging the hole 33 of the receiving cavity 30 with the opening 26 in the top wall 25 of the chamber member 19. The pipetor and apparatus 10 may then be positioned above the gel to be excised. The plunger of the pipetor is pressed to approximately its full insertion in the tubular member 12 to displace air from the lumen 15. The lower cutting edge 21 of the sample removal apparatus 10 is rested on the agarose gel in a tray and pressed down a selected distance. The plunger 16 of the pipetor 11 is then retracted a selected distance within the lumen 15 thereby creating a vacuum in the chamber member 19. The vacuum created holds the section of gel in the chamber member 19 when sample removal apparatus 10 is removed from the tray. The section of gel can then be deposited in another location by placing the lower cutting edge 21 of the sample removal apparatus 10 in the desired location and depressing the plunger 16 of the pipetor 11 a selected distance within the lumen 15. This action decreases the vacuum and releases the section of gel in the desired location.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A sample removal apparatus for excising and ejecting a section of an agarose gel sample from a tray produced by agarose gel electrophoresis using a pipetor of the type having a tubular member with a frusta-conical end portion with a tip aperture in communication with a lumen of the tubular member, the pipetor having a plunger movable in the lumen of the tubular member, the sample removal apparatus comprising:

a chamber member defining an chamber interior, the chamber member having a top with a perimeter wall depending from the top, the perimeter wall having a lower end with a substantially rectangular lower cutting edge defining a cutting perimeter; and a pipetor adapter for receiving a portion of a pipetor, the pipetor adapter having a receiving cavity for receiving the portion of the pipetor, the receiving cavity being formed by a peripheral wall having a lower end mounted to the top of the chamber member;

wherein the perimeter wall has a thickness between an inner surface and an outer surface, the lower cutting edge of the perimeter wall being positioned adjacent to the chamber interior at an intersection of the inner surface of the perimeter wall and the lower end of the perimeter wall, the lower end of the perimeter wall being beveled such that the thickness of the perimeter wall increases from the lower end toward the top.

2. The sample removal apparatus of claim 1 wherein the perimeter wall is comprised of side walls and end walls to define a substantially rectangular cutting perimeter for excising a substantially rectangular section of a sample.

3. The sample removal apparatus of claim 1 wherein the chamber member has a top wall connected to the perimeter wall opposite the lower cutting edge, the top wall having an opening therein in communication with the chamber interior.

4. The sample removal apparatus of claim 1 wherein a plurality of graduations are marked on the perimeter wall and extending from the lower cutting edge toward the top for indicating the volume of the section contained in the chamber interior.

5. The sample removal apparatus of claim 1 wherein the receiving cavity has a hole in fluid communication with an opening in a top wall of the chamber member.

6. The sample removal apparatus of claim 1 wherein the peripheral wall has a generally frusta-conical shape.

7. The sample removal apparatus of claim 1 wherein the peripheral wall of the pipetor adapter has an upper end with a lip formed thereon, the lip having an outer surface protruding from an exterior surface of the peripheral wall for facilitating loading and ejection of the sample.

8. A sample removal apparatus for excising and ejecting a section of an agarose gel sample from a tray produced by agarose gel electrophoresis using a pipetor of the type having a tubular member with a frusta-conical end portion with a tip aperture in communication with a lumen of the tubular member, the pipetor having a plunger movable in the lumen of the tubular member, the sample removal apparatus comprising:

a chamber member defining an chamber interior, the chamber member having a top with a perimeter wall depending from the top, the perimeter wall having a lower cutting edge defining a cutting perimeter; and a pipetor adapter for receiving a portion of a pipetor, the pipetor adapter having a receiving cavity for receiving the portion of the pipetor, the receiving cavity being formed by a peripheral wall having a lower end mounted to the top of the chamber member;

wherein the perimeter wall is comprised of side walls and end walls to define a substantially rectangular cutting perimeter for excising a substantially rectangular section of a sample.

9. The sample removal apparatus of claim 8 wherein the chamber member has a top wall connected to the perimeter wall opposite the lower cutting edge, the top wall having an opening therein in communication with the chamber interior.

10. The sample removal apparatus of claim 8 wherein the lower cutting edge of the perimeter wall is beveled to form a linear edge adapted for moving through gel of a sample.

11. The sample removal apparatus of claim 8 wherein the receiving cavity has a hole in fluid communication with an opening in a top wall of the chamber member.

12. The sample removal apparatus of claim 8 wherein the peripheral wall has a generally frusta-colical shape.

13. The sample removal apparatus of claim 8 wherein the peripheral wall of the pipetor adapter has an upper end with a lip formed thereon, the lip having an outer surface protruding from an exterior surface of the peripheral wall for facilitating loading and ejection of the sample.

14. A sample removal apparatus for excising and ejecting a section of an agarose gel sample from a tray produced by agarose gel electrophoresis using a pipetor of the type having a tubular member with a frusta-conical end portion with a tip aperture in communication with a lumen of the tubular member, the pipetor having a plunger movable in the lumen of the tubular member, the sample removal apparatus comprising:

a chamber member defining an chamber interior, the chamber member having a top with a perimeter wall depending from the top, the perimeter wall having a lower cutting edge defining a cutting perimeter; and a pipetor adapter for receiving a portion of a pipetor, the pipetor adapter having a receiving cavity for receiving the portion of the pipetor, the receiving cavity being formed by a peripheral wall having a lower end mounted to the top of the chamber member;

wherein a plurality of graduations are marked on the perimeter wall and extending from the lower cutting edge toward the top for indicating the volume of the section contained in the chamber interior.

15. The sample removal apparatus of claim 14 wherein the perimeter wall is comprised of side walls and end walls to define a substantially rectangular cutting perimeter for excising a substantially rectangular section of a sample.

16. The sample removal apparatus of claim 14 wherein the chamber member has a top wall connected to the perimeter wall opposite the lower cutting edge, the top wall having an opening therein in communication with the chamber interior.

17. The sample removal apparatus of claim 14 wherein the lower cutting edge of the perimeter wall is beveled to form a linear edge adapted for moving through gel of a sample.

18. The sample removal apparatus of claim 14 wherein the receiving cavity has a hole in fluid communication with an opening in a top wall of the chamber member.

19. The sample removal apparatus of claim 14 wherein the peripheral wall has a generally frusta-conical shape.

20. The sample removal apparatus of claim 14 wherein the peripheral wall of the pipetor adapter has an upper end with a lip formed thereon, the lip having an outer surface protruding from an exterior surface of the peripheral wall for facilitating loading and ejection of the sample.

* * * * *